United States Patent [19]

Wong

[11] 4,348,400
[45] Sep. 7, 1982

[54] PYRIDYLPROPYL ALKYL-SUBSTITUTED BENZOATES AND THEIR USE AS INSECT REPELLENTS

[75] Inventor: Rayman Y. Wong, Richmond, Calif.

[73] Assignee: Stauffer Chemical Company, Westport, Conn.

[21] Appl. No.: 261,423

[22] Filed: May 7, 1981

[51] Int. Cl.³ .................... A61K 31/44; C07D 213/55
[52] U.S. Cl. .................................. 424/263; 546/342
[58] Field of Search ........................ 546/342; 424/263; 546/341

[56] References Cited

U.S. PATENT DOCUMENTS 4,184,040  1/1980  Noteisz et al. ...................... 546/342

OTHER PUBLICATIONS

Hankovszky et al., Journal of Medicinal Chemistry, vol. 9, No. 1, pp. 151–153, Jan. 1966.

*Primary Examiner*—Alan L. Rotman
*Attorney, Agent, or Firm*—Joel G. Ackerman

[57] ABSTRACT

Compounds having the formula

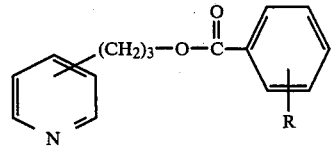

in which R is $C_1$–$C_4$ alkyl, are effective insect repellents.

4 Claims, No Drawings

PYRIDYLPROPYL ALKYL-SUBSTITUTED BENZOATES AND THEIR USE AS INSECT REPELLENTS

This invention relates to repelling insects by the use of novel compounds having the formula

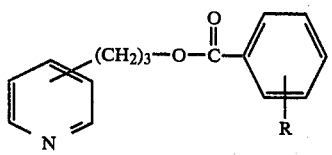

in which R is $C_1-C_4$ alkyl. Preferably R is methyl, most preferably 2-methyl. The compounds are particularly useful for repelling flying insects from lighting and/or feeding.

In general the compounds to which this invention relates may be prepared by reaction of an appropriate pyridyl propanol with an acyl chloride:

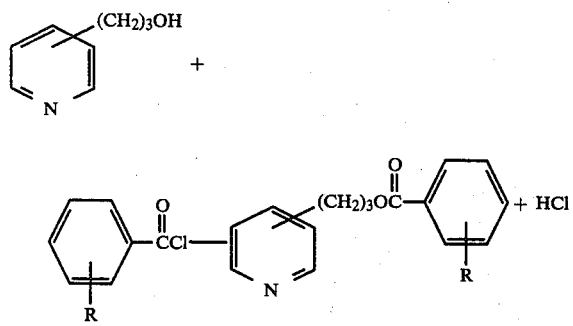

This reaction is generally conducted at temperatures of about 0° to 15° C., in the presence of a solvent such as methylene chloride, and a hydrogen chloride acceptor, preferably an amine such as triethylamine or pyridine.

The following represents an example of the preparation of a compound of this type.

PREPARATION OF 3-(3'-PYRIDYL)-PROPYL-ORTHO-METHYL BENZOATE (COMPOUND 2 HEREIN)

In a flask equipped with a stirrer, was put 5.00 g (0.0364 mole) 3-(3'-pyridyl)-1-propanol, 3.16 g (0.04 mole) pyridine and 50 ml methylene chloride. The resulting clear light yellow solution was cooled to 0° C. with an ice-water bath. There was then added 6.18 g (0.040 mole) o-toluoyl chloride at a rate such that the temperature was maintained at a maximum of 15° C. The cooling bath was then removed and the mixture stirred at room temperature for 1 hour. Ten ml. of water and some methylene chloride were added. The organic phase was separated, washed with three 10 ml. portions of saturated aqueous sodium bicarbonate (the pH of the product was 8); then with water (the pH dropping to 7); then with 10 ml of a saturated sodium chloride solution, and dried with sodium sulfate. The product was then filtered and the solvent removed under vacuum to yield 9.43 g (101.5% of theoretical yield) of a clear yellow oil, $n_D^{30}$ 1.5543. The structure was confirmed by infrared, nuclear magnetic resonance and mass spectroscopy.

The following Table I contains a list of representative compounds of this invention.

Structures of these compounds were similarly confirmed by spectroscopic analyses.

TABLE I

| Compound No. | Position On Pyridine Ring | R | $n_D^{30}$ |
|---|---|---|---|
| 1 | 2- | 2-$CH_3$ | 1.5513 |
| 2 | 3- | 2-$CH_3$ | 1.5543 |
| 3 | 4- | 2-$CH_3$ | 1.5636 |

INSECT REPELLENT TESTS

The compounds in Table I were tested for insect repellency by the following procedures:

Mosquito:

A paper cup filled with pupae of the mosquito *Culex pipiens quinquefasciatus* (Say) was placed in a screened cage and the pupae allowed to emerge into adults. Sugar cubes were then saturated with 1.0 milliliter (ml) of an acetone solution containing 0.1 wt. % of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitoes from the sugar cubes was recorded.

Comparative tests were similarly conducted using the compound N,N-diethyl-m-toluamide, commercially manufactured and employed as an insect repellent, generally known by the generic name "deet". The results of the tests of deet and the compounds of Table I are shown in the following Table II. The numbers in each column represent the number of days of complete repellency observed using the specified concentration.

TABLE II

| Compound No | Days Repelled, 0.1 wt. % |
|---|---|
| 1 | 5 |
| 2 | 4 |
| 3 | 4 |
| deet | 1 |
| control | 0 |

Housefly:

The insect utilized for this test was the housefly, *Musca domestica* (L). One hundred houseflies of mixed sexes were placed in test cages. In each cage was placed a sugar cube saturated with 1.0 ml of acetone containing 1 wt. % of the test compound. The cube was dried and weighed before being placed in the cage. Each cage also contained a water-saturated cotton plug to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube containing only acetone and no test compound, was calculated. The lower the repellency ratio, the greater the repellency of the test compound. The repellency ratios of the test compounds are shown in the following Table III. Values given for the repellency ratio represent an average of from one to three replications per compound.

TABLE III

| Compound | Repellency Ratio: Concentration 1 wt. % |
|---|---|
| 1 | 0.46 |
| 2 | 0.46 |
| 3 | 0.50 |
| deet | 0.60 |

Thus at a concentration of 1% by weight, the three test compounds effected repellency such that the weight loss of sugar cubes treated with those compounds was 50% or less of that of the control (untreated) cubes.

The novel compounds of this invention may be used as insect repellents in either diluted or undiluted form. When used in a diluted form, the compounds may be embodied in compositions containing relatively high or relatively low concentrations of the active compound. For example, the active compound can be incorporated into two relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active components of such compositions or may be used in admixture with other compounds having a similar or different utility. For example, the compounds may be incorporated into creams, lotions, powders, suntan oils, insecticides and other preparations which may contain pesiticidal or other useful substances, as well as into compositions of various types used for treating fabrics or articles of clothing to render them insect repellent. In general, compositions for repellent use may contain from 0.5 to up to 80 weight %, preferably from 2 to about 40 weight %, of the novel active compounds.

Examples of typical formulations employing compounds of this invention are for instance,

EXAMPLE 1: EMULSIFIABLE CONCENTRATE

| Component | Weight % |
|---|---|
| Compound 1 | 53.6 |
| Aromatic Hydrocarbon Solvent | 36.4 |
| Emulsifier | 10.0 |
| Total | 100.0 |

EXAMPLE 2: LOTION

| Component | Weight % |
|---|---|
| Compound 2 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

EXAMPLE 3: ALCOHOL SOLUTION

| Component | Weight % |
|---|---|
| Compound 3 | 53.6 |
| Isopropanol | 46.4 |
| Total | 100.0 |

EXAMPLE 4: ALCOHOL SOLUTION

| Component | Weight % |
|---|---|
| Compound 3 | 80.0 |
| Ethanol | 20.0 |
| Total | 100.0 |

EXAMPLE 5: WETTABLE POWDER

| Component | Weight % |
|---|---|
| Compound 3 | 26.9 |
| Hydrated calcium silicate | 62.1 |
| Sodium lignosulfonate | 5.0 |
| Orzan A (mixture of ammonium lignosulfonate and wood sugars) | 5.0 |
| Wetting agent | 1.0 |
| Total | 100.0 |

What is claimed is:

1. A method of repelling insects from a locus to be protected therefrom, comprising applying to said locus an effective insect repelling amount of a compound having the formula

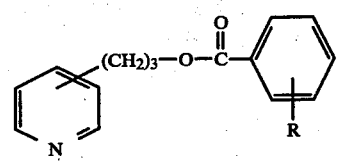

in which R is $C_1$–$C_4$ alkyl.

2. A method according to claim 1 in which R is 2-methyl.

3. A method according to claim 1 in which the compound is applied in an amount effective to repel mosquitos.

4. A method according to claim 1 in which the compound is applied in an amount effective to repel houseflies.

* * * * *